United States Patent [19]

Baldwin et al.

[11] 4,434,032

[45] Feb. 28, 1984

[54] PROCESS FOR MAKING SYMMETRICAL ALKANEDIOLS AND THE BIS-ETHERS THEREOF

[75] Inventors: Maynard M. Baldwin, Columbus; Robert E. Wyant, Delaware, both of Ohio

[73] Assignee: Battelle Development Corporation, Columbus, Ohio

[21] Appl. No.: 487,978

[22] Filed: Apr. 25, 1983

[51] Int. Cl.³ ........................... C25B 3/10; C25B 3/04
[52] U.S. Cl. ................................... 204/72; 204/59 R
[58] Field of Search ........................... 204/59R, 72, 73

[56] References Cited

U.S. PATENT DOCUMENTS 4,253,921 3/1981 Baldwin et al. ........................ 204/72
4,324,625 4/1982 Cumbo .................................. 204/72

FOREIGN PATENT DOCUMENTS 18163 10/1980 European Pat. Off. .

OTHER PUBLICATIONS

Jour. Appl. Electrochemistry 8 (1978) 537–544 by D. Cipris, Electrochemical Reactions of Halohydrins, I. Attempt at Reductive Coupling.

Primary Examiner—John F. Niebling
Attorney, Agent, or Firm—Millard & Cox

[57] ABSTRACT

A process for making symmetrical alkanediols and the bis-ethers thereof by electrochemically coupling the haloalkylethers that are the equivalent of one-half of the symmetrical bis-ether. A symmetrical alkanediol may be obtained from the symmetrical bis-ether. The method significantly increases the yield of alkanediols as for example 1,4-butanediol from electrochemical processes.

26 Claims, 1 Drawing Figure

PROCESS FOR MAKING SYMMETRICAL ALKANEDIOLS AND THE BIS-ETHERS THEREOF

FIELD OF THE INVENTION

The invention relates to improving the yield in the synthesis of symmetrical alkanediols, and more specifically to improving the yields from the electrochemical synthesis of 1,4-butanediol. Additionally, the invention relates to a method for producing symmetrical bis-ethers of alkanediols.

BACKGROUND OF THE INVENTION

The successful electrochemical synthesis of 1,4-butanediol from 2-bromoethanol is demonstrated by U.S. Pat. No. 4,253,921 to Baldwin et al; however, the process therein disclosed produced routine yields of only about 20 percent using the most favorable conditions set forth in that specification.

Product yield in a process of this type is defined as the ratio of the amount of product actually produced to the amount of product that would theoretically have been produced if all of the principal reactant provided and been converted to the desired product. Factors that tend to reduce the yield or lead to inefficiencies in the electrochemical process are side reactions and undesired transitions of intermediately formed radicals and compounds. As an example, in the case of the electrochemical synthesis of 1,4-butanediol, ethylene has been observed evolving from the cathode region of the cell. This may arise from an intermediate radical produced by the electrochemistry of the process being converted. The undesired conversion may be suppressed to some extent by the adjustment of the catholyte pH to not substantially below 7, preferably within the range of 8 to 9 as disclosed in the Baldwin patent. However, even under these favorable conditions yields still remain in the 20 percent range.

It will be understood that the term anolyte refers to the solution contained in the anode compartment of an electrochemical cell, while catholyte refers to the solution retained in the cathode compartment of such a cell.

The use of an organic group substituted for the hydroxyl hydrogen, specifically the acetate of 2-bromoethanol, during the electrochemical synthesis process is disclosed in Cipris (Journal of Applied Electrochemistry, 8, 537-544 and 545-547, 1978). This synthesis involved the use of dimethylformamide as the primary solvent present in the electrolytic cell and utilizes only trace amounts of water. It would be more desirable from a commercial production point of view if an aqueous based solvent could be utilized. The ester derivatives would not be suitably stable in an aqueous environment, particularly at the high pH values cited in U.S. Pat. No. 4,253,921 to Baldwin et al., since such derivatives would be extensively hydrolysed under those conditions.

Therefore, there is a need to improve the yields of the electrochemical type coupling process leading to the production of 1,4-butanediol and other symmetrical alkanediols in order to make the process commercially attractive.

Since it is believed that an aqueous based electrochemical system will have considerably greater industrial potential than a system utilizing no water or only trace amount thereof, the work on improving the yields of the product 1,4-butanediol concentrated on utilizing an electrochemical cell environment corresponding to the most successful system identified in U.S. Pat. No. 4,253,921 to Baldwin et al.

SUMMARY OF THE INVENTION

Therefore, the present invention provides an improved method for making symmetrical bis-ethers of symmetrical alkane diols by the electrochemical cathodic coupling of a mono-ether one moiety of the ether comprising a haloalkyl group wherein the halogen is either bromine or iodine, and the halogen is separated from the ether oxygen by no more than six carbon atoms and not less than 2 carbon atoms; the second moiety of the ether being coupled being a radical selected from the group consisting of: a C4 to C10 alkyl radical having a tertiary carbon adjacent the ether oxygen atom, or a five-membered or six-membered oxacyclic ring having a ring carbon adjacent the ether oxygen atom and a ring oxygen atom adjacent to said ring carbon atom. The electrolytic coupling takes place in an aqueous electrolytic bath having a pH not substantially below 7 and comprising an electrolyte.

The present invention also provides an improved method for making symmetrical alkanediols from haloalkanols, the halogen being either bromine or iodine and being separated from the hydroxyl group by not more than six carbon atoms nor less than two carbon atoms, which involves replacng the hydroxyl hydrogen with an organic group selected from the group consisting of: a C4 to C10 alkyl radical having a tertiary carbon adjacent the ether oxygen atom, or a five-member or six-membered oxacyclic ring having a ring carbon attached to the hydroxyl oxygen of said haloalkanol and a ring oxygen adjacent said ring carbon; cathodic coupling of the ether to obtain a bis-ether, followed by de-etherifying the bis-ether to give a symmetrical alkanediol.

DETAILED DESCRIPTION OF THE INVENTION

Figure 1:
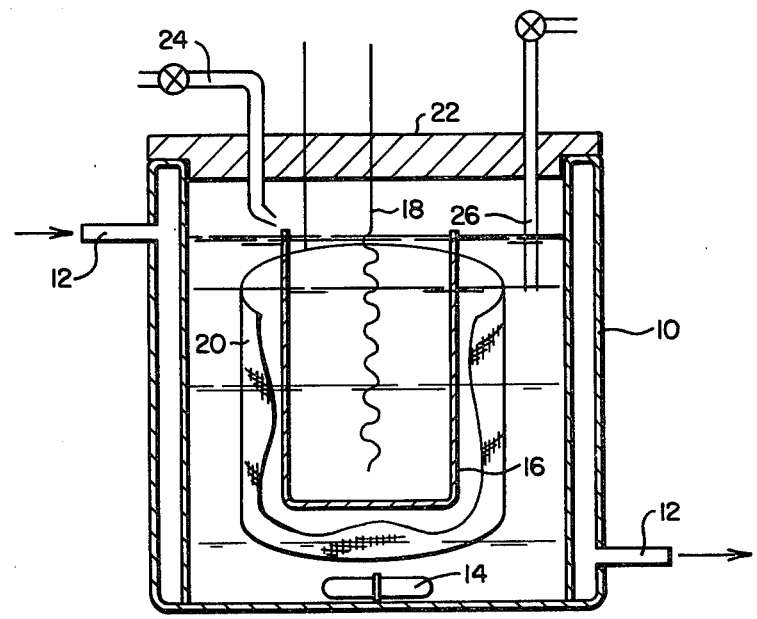

The instant process involves the preparation of a derivative compound of the haloalkanol starting material (preferably a 2-bromoethanol) wherein the hydroxyl hydrogen is replaced by an organic group (forming preferably a 2-bromoethyl ether). The characteristics of the organic group are that the ether bond be stable under the subsequent electrochemical coupling conditions, and such that the coupling reaction will occur in only one way thereby producing as pure a product as possible. Additional requirements of the organic group are that it will be suitably cleaved from the resulting symmetrical bis-ether leaving the hydroxyl oxygen unhindered on the final product and thereby restoring the original hydroxyl groups. Due to the aqueous alkaline environment of the preferred catholyte conditions, an esterified derivative compound will not produce suitable results since the ester group is easily hydrolized in the alkaline environment thereby causing the derivative to decompose into the original haloalkanol and a salt of the acid used to form the ester.

The substitution of the selected organic group for the hydroxyl hydrogen produces an ether wherein one moiety of the ether is the haloalkyl from the original haloalkanol, the halogen being either bromine or iodine and being separated from the ether oxygen by no more than six carbon atoms or less than two carbon atoms. The other moiety of the derivative ether compound is a radical selected from the group consisting of a C4 to C10 alkyl radical having a tertiary carbon adjacent to and attached to the above said ether oxygen, or a five-membered or six-membered oxacyclic ring having a ring carbon bonded to the exo-ring ether oxygen atom and a ring oxygen atom adjacent the ring carbon atom. The systems used and described in the examples below utilize a tertiary butyl group wherein the t-butyl haloalkyl ether is synthesized by the pressurized reaction of isobutylene with the haloalkanol. The other preferred organic groups is tetrahydropyranyl, the tetrahydropyranyl haloalkyl either being synthesized by the reaction of dihydropyran with the haloalkanol; and similarly, a tetrahydrofuranyl ether being the etherified product of the haloalkanol reaction with dihydrofuran. Additionally, the etherification of the haloalkanol starting material can be achieved by various other conventional methods which will be apparent to those skilled in the art. An additional example is the reaction of dicyclopentadiene with a 2-bromoethanol to form dihydro-exo-dicyclopentadienyl 2-halo ether and coupling this mono-ether to yield 1,4 bis (dihydro-exo-dicyclopentadienyl) butyl ether.

The 2-bromoethyl ethers of organic groups meeting the above criteria were sufficiently stable under the electrochemical cell conditions utilized to allow increased yields of the cathodic coupled products to be obtained.

It will be appreciated that any one of the methyl groups existing on the tertiary butyl group could be replaced with a one to six carbon alkyl group without adversely affecting the action of the tertiary carbon bonded to the ether oxygen. The only proviso is that the tertiary carbon containing group not be so complex as to interfere spatially with the electrochemical coupling reaction, or the subsequent cleaving reaction which is described more fully below.

The mechanism involved in obtaining increased coupling yields from the derivative mono-ether reactants over those yields that were obtained from the direct electrochemical cathodic coupling of a haloalkanol starting material is not well understood. One possibility for the mechanism is that the effect of the substituent group which replaces the hydroxyl hydrogen involves electron displacement in the chemical bonds of the compound, making the carbon-halogen bond weaker thus promoting the coupling reactions. However, if this were the sole mechanism one would not expect a tertiary butyl group and a tetrahydropyranyl group to have similar effects in improving the yields from the coupling reaction, but in fact yields are increased using either of these organic groups in the mono-ether.

Another suggested mechanism is that the hydroxyl group is more likely to leave the dehalogenated radical of the haloalkanol than the ether group is likely to leave the dehalogenated radical of the mono-ether. However, again the prior art teaches that a hydroxyl group and ether group are both very poor leaving groups and therefore would not show different behavior. The experimental results support this.

For the purposes of obtaining results which are easily compared, the "optimum" conditions disclosed in the Baldwin, et al patent were selected as the conditions under which the mono-ether cathodic coupling reaction would be carried out. It will be appreciated that more advantageous conditions in the electrochemical cell as for example modification of the catholyte by changing solvents, by adjusting electrolytes, by adjusting the temperature and other variables may result in even greater improvement in the yield using the ether coupling concept herein disclosed. The best results were obtained, under the best conditions of the Baldwin patent, in the coupling of tetrahydropyranyl 2-bromoethyl ether. A significant improvement in yield was obtained using the tertiary butyl 2-bromoethyl ether, but as is discussed below some modifications in the cell conditions are clearly necessary in order to obtain optimal results using the tertiary butyl group route. As in the Baldwin, et al. patent, the pH is maintained by the use of a suitable base that is adequately soluble in the solvent system. Suitable bases include alkali metal bases such as alkali metal hydroxides, ammonium bases such as ammonium hydroxide, quaternary ammonium bases such as quaternary ammonium hydroxides, and the like. The better yields were obtained with ammonium compounds in the catholyte.

The derivatives which are ethers of the haloalkanol are then coupled in an aqueous electrochemical cell to form symmetrical bis-ethers by the dehalogenation of the haloalkyl ether with the coupling taking place at the sites of the displaced halogen atoms. This results in a "head-to-head" dimerization reaction that is electrochemically induced in an aqueous phase electrochemical cell. The resulting coupled compound is said to be symmetrical. Symmetrical as it is used herein, refers to the products of the electrochemical coupling or dimerization in that two identical starting groups have been joined "head-to-head" to produce a single molecule that has the same molecular structure on each end and is therefore symmetrical about the point at which the starting materials were joined.

Another consequence of using ether derivatives in place of an haloalkanol as the materials to be coupled is a more favorable situation for isolating the coupled product from the catholyte which nominally contains an alcohol and water or other solvents. Extraction of the catholyte with organic solvents can be expected to be more effective with the bis-ethers. In addition, ethers of this sort are expected to form azetropes with water or in some cases ternary azeotropes with ethanol and water which also lead to easier product separation with the avoidance of distillation of appreciable quantities of water. Another area of improvement of the process would be anticipated as being the replacement of ethanol with other organic water-miscible solvent in the catholyte wherein such solvents produce the more advantageous separation conditions.

After the bis-ethers are separated from the catholyte, they are subjected to suitable cleaving or de-etherification conditions as are conventional in the art. Such de-etherification conditions are preferred to be applied in the presence of some water and to be as mild a condition as possible to avoid the dehydration of the diol to yield for example tetrahydrofuran (THF) in the case of 1,4butanediol. The preferred method for cleaving the groups from the opposite ends of the bis-ether is by passing the bis-ether over a suitable acid catalyst at elevated temperatures in the presence of steam or water. While THF may be a desirable product in some circumstances, the desired product under these conditions is the symmetrical alkanediol, and therefore the presence of water may be necessary if dehydration is to be avoided.

It will be appreciated that although passing a bis-ether azeotrope with water over a suitable acid catalyst tends to suppress THF formation in the case of 1,4-butanediol, the cleaved end groups may tend to form alcohols rather than the original olefin starting materials. It would be most desirable to recover isobutylene in the case of the t-butyl group and dihydropyran in the case of the tetrahydropyranyl group. However, the presence of water may tend to hydrate the double bonds producing alcohols. Of course, the conversion of such alcohols back into the desired olefins is but a simple dehydration process well known to those skilled in the art. Recovery of the original olefin reactants allows for the development of a recycle process producing symmetrical alkanediols with the materials required for the production of the derivative group being recycled with little loss during the process.

IN THE EXAMPLES

The electrolytic cell used in the examples was a jacketed glass vessel 10 having cooling water circulated through the jacket 12. Additionally, a magnetic stirring bar 14 was placed in the bottom of the vessel 10 in order to promote temperature control throughout the cell, and to obtain good contact of the reactant mono-ether with the cathode. A porous ceramic cup 16 separates the catholyte from the anolyte. The porosity is such as to allow the passage of ions but not of molecules, particularly bromine or of the coupled product and starting derivative materials in the catholyte. A coiled platinum wire serves as the anode 18, while the cathode 20 was a cylindrical plated wire mesh screen surrounding and spaced apart from the porous ceramic cup 16. The entire glass vessel 10 was then fitted with a teflon cup 22 that was sealed utilizing silicon lubricant since it was desired to take a gas sample from the cathode region by means of probe tube 24 to analyze for ethylene production, or other gas evolving from the catholyte. The cover plate 22 contained a sampling device 26 to obtain catholyte samples for analysis and pH measurements. The sampling device 26 also served as a means for adding materials to the catholyte such as bases for pH adjustment. In each experiment a separate and new plated cathode was utilized. That electrode 20 was manufactured utilizing a copper-bronze screen 14×18 mesh formed into a cylindrical shape 1.25 inches (31.75 mm) in diameter and a height of 1.75 inches (44.45 mm). The screen was plated in a 2.5 liter bath comprising 105 g. per liter of $CuSO_4.5H_2O$ and 52 g. per liter of sulfuric acid (1.84 density) with appropriate quantities of distilled water. The screen was electroplated in the bath for a period of 3 hours and 40 minutes using 3.9 amps at approximately 1.5 volts. It was discovered that either pickling or hot alkaline treatment of the screen prior to electroplating produced undesirable results and therefore these practices should be avoided. After electroplating, the plated electrode should be stored under distilled water until time for use.

EXAMPLE 1 t-Butyl ether of 2-bromoethanol which will later be utilized as the derivative reactant in the coupling reaction in the electrolytic cell, is prepared by the following procedure. A 300 ml. 316 stainless steel stirrable autoclave was charged with a mixture comprising 50 ml.(88 g., 0.71 moles) of 2-bromoethanol and 5 g. of Amberlyst 15 ion exchange resin. The reaction temperature was 26° C. The autoclave was pressurized with iso-butylene to 12 psig. Stirring was started and the pressure rapidly went to 0. The autoclave was then pressurized to 12 psig. and as reaction progressed the pressure rapidly decreased to 3 psig. The batchwise reaction was continued until upon pressurization with iso-butylene to 12 psig. the pressure in the autoclave was maintained at 12 psig. for a full two-hour period. A two-hour time period without pressure change indicated that no further gas uptake or reaction was occurring. The autoclave was then opened and emptied. Product weight was 125 g. and a gas chromatographic analysis showed only one major peak that did not correspond to the 2-bromoethanol peak, showing essentially 100 percent converion to 2-bromoethyl t-butyl ether. The derivative, the t-butyl 2-bromoethyl ether, was recovered by filtering the catalyst followed by vacuum distillation of the filtrate. Vacuum distillation at aproximately 60°-70° C. is required since the t-butyl ether decomposes at the temperatures required for atmospheric distillation, approximately 140° C., to the starting materials iso-butylene and 2-bromoethanol. This mono-ether was subjected to the electrochemical coupling reaction.

Since the cathode and anode compartments are separated, separate catholyte and anolyte solutions are prepared as follows:

catholyte—16.6 ml of distilled water, 33.8 ml ethanol, 2.73 g. of ammonium chloride, 3.47 ml. of ammonium hydroxide, and 5.35 ml. 2-bromoethyl t-butyl ether from the above preparation. The total volume of the catholyte without the ether was 54 ml., anolyte—10 ml.of 10 percent ammonium chloride in distilled water.

The electrode was placed in the cell and the catholyte solution added less the ether. A pre-electrolysis and purging with argon gas was performed for 20 minutes at 20.6 amp and approximately 4.5 volts. Slight bubbling around the electrode occured during this pre-electrolysis period.

The 2-bromoethyl t-butyl ether was then added and the solution became cloudy initially, but after approximately 10 minutes the solution cleared. The temperature of the bath was approximately 78° F. initially but was cooled down to the desired 70° F. early in the reaction and maintained at 70° F. throughout the balance of the run. Current was maintained at 0.6 amps and approximately 4.5 volts. The anolyte became yellow in color and there was slight bubbling around the anode during the run. After approximately one hour the pH was checked and determined to be approximately 8. At this point additional ammonium hydroxide was added to increase the pH to approximately 10. After 1½ hours of total run time the anolyte had turned to a yellow-orange color and the pH was now approximately 9 in the catholyte. With the current being maintained at 0.6 amps and approximately 4.5 volts the electrolysis proceeded. After 2½ hours the electrolysis was stopped. At this time the anolyte had turned a fully brown color. The final volume of the catholyte was 50 ml.

Analysis of the catholyte by gas chromatographic technique showed that the only significant organic compounds present were the alcohol solvents, a small amount of starting material and the bis-ether product. The concentration of the bis-ether product in the catholyte was determined by use of an external standard in measurement of the gas chromatographic results. The yield was calculated from the amount of mono-ether in the catholyte at the start of the run and the amount of bis-ether product obtained, with the following results:

| Run No. | % Bromoethanol | % Butanediol | % Starting Derivative | % Bis-ether |
|---|---|---|---|---|
| 1 | — | — | Approx. 5% | 24.0% |
| 2 | — | — | 5% | 24.3% |

EXAMPLE II

The preparation of the tetrahydropyanyl ether of 2-bromoethanol which is the other major derivative to be electrolyzed in the examples below was accomplished by the following procedure: A one liter Erlenmeyer flask was charged with: 68.0 g. (0.54 moles) of 2-bromoethanol, 200 ml of dichloromethane and 400 mg. of p-toluene-sulfonic acid. The flask was surrounded by an ice-salt bath and the flask contents stirred with a magnetic stirring bar. The following solution was added dropwise over 1¼ hour period of time: 50 g. (0.60 moles) of dihydropyran in 178 ml of dichloromethane. The solution was then stirred and allowed to warm to room temperature following the dropwise addition. The resultant material was washed with a 10 percent sodium bicarbonate solution. Two separate washings of 200 ml. each were performed. The material was then dried over anhydrous magnesium sulphate, filtered and the solvent evaporated. This resulted in 122.8 g of a yellow liquid which was distilled under reduced pressure conditions at approximately 15 mm Hg+1 mm Hg, into three cuts. The first cut was 10.1 g. of a white liquid with a cutoff high temperature of 73° C., the second cut was 41.5 g. in the temperature range 73°-86° C., the third cut was 36.5 g. of a white liquid in the temperature range 86°-98° C.; 3.2 g. of a brown liquid residue remained which was discarded. Fraction cuts 2 and 3 in the temperature range 73°-98° C. were retained as the product. This resulted in a 69.1 percent yield of the tetrahydropyanyl ether of 2-bromoethanol. This product was analyzed by gas chromatographic analysis. The distilled tetrahydropyanyl bromoethyl ether product was retained for later use in the cathodic coupling reaction.

The example continues with the electrocoupling of the 2-bromoethyl tetrahydropanyl ether. The cathode utilized is made by the same method as previously described. The following solutions were used:

catholyte—16.6 ml distilled water, 33.8 ml. ethanol, 2.73 g. ammonium chloride, 3.47 ml. ammonium hydroxide and 5.35 ml or 7.24 g. of the derivative ether, anolyte—10 ml. of 10 percent of ammonium chloride solution in water.

The initial pH of the catholyte was measured at 8.4 and then adjusted by the addition of ammonium hydroxide to 8.7.

Again as before the catholyte solution less the derivative ether was added to the cathode compartment, and the anolyte solution added to the anode compartment. The initial volume of the catholyte was 54 ml. Twenty minutes of pre-electrolysis and argon purging was conducted at 0.6 amps at approximately 4.3 volts. No ether derivative was present during the pre-electrolysis period. There was good bubbling around the cathode and the solution remained clear. The cell temperature was 70° F., controlled and maintained by the circulating bath.

When the ether derivative was added the solution very very slightly bubbled. Almost immediately the anolyte solution turned a very light yellow. After 30 minutes with the current remaining at 0.6 amps and the voltage remaining at approximately 4.3 volts the pH was again adjusted since it had dropped to 8.2. Adjustment was by the addition of 20 drops of ammonium hydroxide solution returning the pH to approximately 8.7. After one hour at constant current and voltage, the pH had fallen to 8.4 and again 20 drops of ammonium hydroxide was added; the anolyte now appeared a yellow-brown color. After 1½ hours (90 minutes) with the current and voltage remaining constant the pH had again dropped B 8.4 and the anolyte had now turned a brown color. The slight bubbling around the cathode remained constant throughout the entire run. At the end of two hours of electrolysis the current and voltage were still at 0.6 amps and approximately 4.3 volts; the pH had leveled to 8.4 and the anolyte remained the previously described brown color. The electrolysis was terminated at the end of two hours. The final volume of the catholyte was 54 ml.

The catholyte solution was analyzed by gas chromatographic techniques as described in Example I above. Again, the only significant organic compounds present were the alcohol solvents, a small amount of the staring mono-ether material and the bis-ether product. Yield was again calculated based on the amount of mono-ether in the catholyte at the start of the run and the amount of bis-ether product obtained, with the following results:

| Run No. | % Bromoethanol | % Butanediol | % Starting Derivative | % Bis-ether |
|---|---|---|---|---|
| 3 | — | — | Approx. 5% | 43.6% |

The bis-ether is herein called 1,4-bis(tetrahydropropanyl-2-oxy) butane, (the Chemical Abstracts lists this compound as 2,2'(tetramethylenedioxy)bis(tetrahydro-2H-pyran) with the registry number 15057-13-3.

Additionally the method was checked to determine the value of a 2-chloroethylt-butyl ether in a coupling reaction. The same conditions were established as in Example I. However there was no yield, no production of the bis-ether when chlorine was utilized as the halogen. This reconfirmed the negative results of previous research that, the only satisfactory results occur when the halogen is either bromine or iodine.

An additional run was made using a derivative product prepared by reacting propionaldehyde with 2-bromoethanol yielding an acetal. When the catholtye of the electrochemical cathodic coupling reaction with the acetal was analyzed by gas chromatographic techniques as previously described, significant quantities of many different organic compounds were found to be present in the catholyte. This is apparently because the acetal prepared can couple in different ways. Therefore, the utilization of such an organic group is not recommended and was not pursued further in this testing.

Utilizing tetrahydrofuranyl as a derivative group will have similar results to those achieved by the tetrahydropyranyl group. In the case of both derivatives a ring carbon adjacent to the ring oxygen directly bonds to the ether oxygen of the ethoxy group, therefore similar positive results will follow because of the similarity of the pyranyl and furanyl groups. The bis-ether obtained from the cathodic coupling of the mono-ether of 2-bromoethanol is herein called 1,4-bis(tetrahydrofuranyl-2-oxy)butane. This bis-ether has a Chemical Abstracts Registry No. of 76702-30-2.

On the basis of only the amount of starting material consumed, the corrected yields of t-butyl bis-ether would be about 30 percent and of the tetrahydropyranyl bis-ether about 48 percent. The bubbling occuring at the cathode in all of the runs may be attributed to the production of ethylene. Analysis of a gas sample by gas chromatographic technique showed an ethylene content of 10 percent, about 0.5 percent ethane, and no appreciable content of other hydrocarbons. Attempts to obtain gas samples not diluted by air or to collect sufficiently pure samples to determine rate, and thereby amount of gas production were unsuccessful.

It will be appreciated that the conditions within the electrolytic cell, and more specifically of the catholyte can be altered and that different results from those obtained herein are possible when those conditions are so altered. The conditions of temperature, solvent, current and voltage requirements all may have some effect on the operation and yield from such an electrochemical cell. The cell conditions in the experiments conducted herein were maintained at a constant level for the purposes of comparison, and it is anticipated that a more optimal set of cell operating conditions can be arrived at by appropriate experimentation. It is additionally clear that the concept of coupling mono-ethers to produce bis-ethers which can then be cleaved to produce the desired symmetrical alkanediol will work equally well in improving the yields under the conditions outlined in Cipris and also in the conditions disclosed in U.S. Pat. No. 4,324,625 to Cumbo.

Since it was discovered that the tertiary butyl derivative is extremely temperature sensitive requiring vacuum distillation even for the most rudimentary purification, it is postulated that the yields utilizing the tertiary butyl group will be considerably increased if the temperature of the electrochemical coupling reaction is considerably reduced. Apparently the stability of the tertiary butyl derivative is increased by a reduction in temperature. The temperature was maintained at 70° F. during the examples performed herein since that temperature corresponded to the previously used conditions outlined in U.S. Pat. No. 4,253,921 that was previously discussed. However even at 70° F. the tetrahydropyranyl group produced considerably increased yield over those previously attained without the use of a derivative group.

In addition to a process whereby the yields of alkanediol are enhanced by the use of substituent groups forming ether derivatives which are subsequently dehalogenated and coupled, the symmetrical bis-ethers produced by the coupling reaction have utility in themselves. Such symmetrical bis-ethers may be used as fuel additives, hydraulic fluids, lubricant additives, solvents and also have possible use as plasticizers for synthetic resins, especially polyacetal resins. Thus, of interest are bis-ethers that may be produced by the electrochemical cathodic coupling process herein disclosed wherein the substituent organic group is not easily cleaved from the resultant bis-ether, but where the bis-ether is the primarily sought compound. Therefore the required characteristics of such a substituent organic group would be the stability of the mono-ether and its free radical during the electrochemical coupling process and not its ability to be cleaved to form the symmetrical alkanediol.

It will be appreciated that numerous changes and modifications may be made in the above-described embodiments of the invention without departing from the scope thereof. Accordingly, the foregoing description is to be construed in an illustrative and not in a limitative sense, the scope of the invention being defined solely by the appended claims.

We claim:

1. A method for making a bis-ether of a symmetrical alkanediol comprising the steps of: electrochemically coupling an ether in an aqueous electrolytic bath having a pH not substantially below 7 and comprising an electrolyte, one moiety of said ether being a haloalkyl group wherein said halogen is bromine or iodine and is separated from the ether oxygen by no more than six carbon atoms and not less then two carbon atoms, the second moiety of said ether being selected from the group consisting of: a $C_4$–$C_{10}$ alkyl radical having a tertiary carbon adjacent the ether oxygen atom, a 5-membered or a 6-membered oxacyclic ring having a ring carbon adjacent the ether oxygen atom and a ring oxygen atom adjacent said ring carbon atom.

2. The method according to claim 1 wherein said first moiety is a 2-bromoethyl group.

3. The method according to claim 1 wherein said second moiety is a t-butyl group.

4. The method according to claim 1 wherein said bis-ether is 1,4-bis(t-butoxy)butane.

5. The method according to claim 1 wherein said second moiety is a tetrahydropyranyl group.

6. The method according to claim 1 wherein said bis-ether is 1,4-bis(tetrahydropyranyl-2-oxy)butane.

7. The method according to claim 1 wherein said second moiety is a tetrahydrofuranyl group.

8. The method according to claim 1 wherein said bis-ether is 1,4-bis(tetrahydrofuranyl-2-oxy)butane.

9. The method according to claim 1 wherein said electrolytic bath further comprises a water-soluble organic solvent.

10. The method according to claim 9 wherein said organic solvent is an alcohol or a glycol.

11. The method according to claim 10 wherein said alcohol is ethanol.

12. The method according to claim 1 wherein water comprises no greater than 30% by weight of the electrolytic bath.

13. The method according to claim 1 wherein the temperature of said electrolytic bath is maintained at a temperature substantially below 100° F.

14. The method according to claim 13 wherein the temperature of said bath is maintained in the range between about 20° F. and about 70° F.

15. The method according to claim 1 wherein said pH is maintained between about 8 and about 10 during said electrochemical coupling.

16. The method according to claim 1 wherein said electrolyte is an amine salt, an ammonium salt, or a quaternary ammonium salt.

17. The method according to claim 16 wherein said electrolyte is ammonium chloride.

18. The method according to claim 16 wherein said cathode has a copper surface plated onto a substrate.

19. The method according to claim 1 further comprising the steps of:
preparing said ether by the etherification of a haloalkanol an unsaturated hydrocarbon or unsaturated oxacyclic compound.

20. The method according to claim 19 wherein said unsaturated hydrocarbon has the general formula:

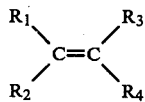

wherein $R_1$ and $R_2$ represent, independently of each other, a methyl or ethyl group, whilst $R_3$ represents a hydrogen atom or a methyl group and $R_4$ represents an hydrogen atom.

21. The method according to claim 20 wherein said unsaturated hydrocarbon is iso-butylene.

22. The method according to claim 19 wherein said unsaturated hydrocarbon is dicyclopentadiene.

23. The method according to claim 19 wherein said etherification reaction takes place in the presence of a catalyst.

24. The method according to claim 1 for making a symmetric alkanediol by further comprising the steps of: de-etherifying said bis-ether.

25. The method according to claim 24 wherein said de-etherifying step is conducted in an aqueous environment.

26. The method according to claim 24 wherein said de-etherifying step takes place in the presence of an acid catalyst at an elevated temperature.

* * * * *

UNITED STATES PATENT OFFICE
CERTIFICATE OF CORRECTION

Patent No. 4,434,032   Dated February 28, 1984

Inventor(s) Maynard M. Baldwin and Robert E. Wyant

It is certified that error appears in the above-identified patent and that said Letters Patent are hereby corrected as shown below:

Column 1, line 23: Should read --- had --- rather than "and";

Column 2, line 28: Should read --- replacing --- rather than "replacng";

Column 5, line 30: Should read --- cap --- rather than "cup";

Column 5, line 66: Should read --- then repressurized --- rather than "then pressurized";

Column 6, line 9: Should read --- conversion --- rather than "converion";

Claim 19, column 10, line 65: Should read --- haloalkanol with an --- rather than "haloalkanol an".

Signed and Sealed this

Twenty-sixth Day of June 1984

[SEAL]

Attest:

GERALD J. MOSSINGHOFF

Attesting Officer   Commissioner of Patents and Trademarks